US010502702B2

(12) United States Patent
Hong (10) Patent No.: US 10,502,702 B2
(45) Date of Patent: Dec. 10, 2019

(54) CAPACITOR TYPE HUMIDITY SENSOR

(71) Applicant: Magnachip Semiconductor, Ltd., Cheongju-si (KR)

(72) Inventor: Ju Hyun Hong, Cheongju-si (KR)

(73) Assignee: MagnaChip Semiconductor, Ltd., Cheongju-si (KR)

( * ) Notice: Subject to any disclaimer, the term of this patent is extended or adjusted under 35 U.S.C. 154(b) by 399 days.

(21) Appl. No.: 14/584,006

(22) Filed: Dec. 29, 2014

(65) Prior Publication Data

US 2016/0003758 A1    Jan. 7, 2016

(30) Foreign Application Priority Data

Jul. 2, 2014  (KR) .................. 10-2014-0082663

(51) Int. Cl.
*G01N 27/22*    (2006.01)

(52) U.S. Cl.
CPC ................... *G01N 27/223* (2013.01)

(58) Field of Classification Search
CPC .. G01N 27/223; G01N 27/224; G01N 27/227; G01F 23/26; G01F 23/263; G01F 23/266; G01F 23/268
USPC .... 73/29.01, 29.02, 29.05, 31.05, 31.06, 74, 73/335.02, 335.04, 335.06; 324/658, 663, 324/664, 665, 686, 689; 361/286, 296
See application file for complete search history.

(56) References Cited

U.S. PATENT DOCUMENTS

| 7,032,448 | B2 | 4/2006 | Hamamoto | |
|---|---|---|---|---|
| 7,594,435 | B2* | 9/2009 | Sudo | G01N 27/223 73/335.02 |
| 9,594,041 | B2* | 3/2017 | Koo | G01N 27/223 |
| 2006/0037393 | A1* | 2/2006 | Itakura | G01D 5/24 73/335.04 |
| 2006/0096371 | A1* | 5/2006 | Isogai | G01N 27/223 73/335.04 |
| 2007/0186649 | A1* | 8/2007 | Sudo | G01N 27/223 73/335.04 |
| 2007/0234801 | A1* | 10/2007 | Weber | G01N 27/12 73/335.02 |
| 2011/0146400 | A1* | 6/2011 | Humbert | G01N 27/223 73/335.04 |
| 2011/0296912 | A1* | 12/2011 | Merz | G01M 3/045 73/335.05 |
| 2012/0304742 | A1* | 12/2012 | Cummins | G01N 27/121 73/31.06 |
| 2014/0196522 | A1* | 7/2014 | Borini | G01N 7/00 73/29.03 |

(Continued)

*Primary Examiner* — Steven L Yeninas
(74) *Attorney, Agent, or Firm* — NSIP Law (57) ABSTRACT

A capacitor type humidity sensor may include a semiconductor substrate comprising a humidity sensing region and a peripheral circuit region, a sensing capacitor disposed on the humidity sensing region and the sensing capacitor comprising a humidity sensitive layer, a dielectric layer made of a material different than from the humidity sensitive layer, and a reference capacitor configured to provide a reference capacitance value, wherein the sensing capacitor and the reference capacitor are disposed on different planes from each other. A reference capacitor is disposed at an arbitrary region under a sensing capacitor among a humidity sensing region or at a peripheral circuit region. The reference capacitor is a metal-insulator-metal (MIM) capacitor or a polysilicon-insulator-polysilicon (PIP) capacitor.

25 Claims, 8 Drawing Sheets

(56) References Cited

U.S. PATENT DOCUMENTS

2014/0366630 A1* 12/2014 Franz .................. G01N 27/223
73/335.04
2015/0153296 A1* 6/2015 Gryska ................ G01N 27/121
73/335.04

* cited by examiner

CAPACITOR TYPE HUMIDITY SENSOR

CROSS-REFERENCE TO RELATED APPLICATIONS

This application claims the benefit under 35 U.S.C. § 119(a) of Korean Patent Application No. 10-2014-0082663 filed on Jul. 2, 2014, in the Korean Intellectual Property Office, the entire disclosure of which is incorporated herein by reference for all purposes.

BACKGROUND

1. Field

This following description relates to a capacitor type humidity sensor that may be aligned under a sensor capacitor. A reference capacitor provided in a humidity sensor is replaced with an MIM (metal-insulator-metal) capacitor or a PIP (polysilicon insulator polysilicon) capacitor.

2. Description of Related Art

As smart devices are commercialized, various sensors embedded to the device are suggested. For example, a humidity sensor may be embedded to recognize an ambient humidity.

Humidity sensors are divided into resistive humidity sensors and capacitive humidity sensors. A resistive humidity sensor measures humidity based on a change in resistance that is changed by humidity. Resistive humidity sensors are widely used because resistance humidity sensors tend to be price competitive in comparison to capacitive humidity sensors.

Recently, capacitive humidity sensors are manufactured on a semiconductor substrate in a one-chip form. Accordingly, it may be possible to obtain capacitive humidity sensors that are more price competitive than resistive humidity sensors. As a result, the use of capacitive humidity sensors is increasing. Further, capacitive humidity sensors may exhibit higher reliability, and may exhibit more linear sensor features and low affect due to temperature change, in comparison to resistive humidity sensors. A capacitive humidity sensor may operate as a capacitor type device having a humidity sensitive material such as polymer or ceramic absorbs moisture, which has permittivity that is changed in the presence of moisture. That is, a humidity sensitive layer for sensing humidity may be present inside the device, and the permittivity of the humidity sensitive layer may change when moisture is introduced through the humidity sensitive layer. As a result, the capacitance is changed, and the capacitance may be determined to determine a level of humidity.

There are many kinds of capacitors to measure a change of humidity. It is important to minimize a chip area as much as possible. Furthermore, manufacturing costs of a humidity sensor need to be minimized. The disclosure of U.S. Patent Application Publication No. US 2004/0182153 A1 to Hamamoto ("Hamamoto") is incorporated herein in its entirety by reference.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

An object of the present disclosure is to provide a capacitor type humidity sensor in which a reference capacitor is disposed at an arbitrary position under a sensing capacitor to reduce the entire size of the humidity sensor.

Another object of the present disclosure is that by selecting an MIM capacitor or a PIP capacitor as the reference capacitor, the manufacturing costs of the sensor chip can be reduced.

In one general aspect, there is provided a capacitor type humidity sensor including a humidity sensing region and a peripheral circuit region, a sensing capacitor disposed on the humidity sensing region and the sensing capacitor comprising a humidity sensitive layer, a dielectric layer made of a material different than the humidity sensitive layer, and a reference capacitor configured to provide a reference capacitance value, wherein the sensing capacitor and the reference capacitor are disposed on different planes from each other The reference capacitor may be aligned under the sensing capacitor.

An MIM (metal insulator metal) capacitor in the form of array may be used as the reference capacitor. A PIP (polysilicon insulator polysilicon) capacitor in the form of an array may be used as the reference capacitor.

The sensor may include a feedback capacitor configured to provide a feedback capacitance value ($C_f$), wherein a dielectric layer of the feedback capacitor is made of a different material from the humidity sensitive layer.

The feedback capacitor may be configured to accumulate a charge that corresponds to capacitance differences ($C_s$-$C_r$) generated in the sensing capacitor and the reference capacitor.

The humidity sensitive layer may extend to an upper portion of a passivation layer disposed on the peripheral circuit region.

The humidity sensitive layer may be exposed to the atmosphere.

In another general aspect, there is provided a capacitor type humidity sensor including a humidity sensing region that is exposed to the atmosphere, and a peripheral circuit region configured to process a digital signal, wherein the humidity sensing region comprises a sensing capacitor, and a reference capacitor disposed on a different plane than the sensing capacitor and aligned under the sensing capacitor.

The peripheral circuit region may be configured to process a signal detected by the humidity sensing region to output a detected humidity.

The peripheral circuit region may comprise a reference voltage block, a temperature sensing block, a Vdd power supply block, a gain control amp (GCA) block, and at least one signal control block.

The sensing capacitor may include a first electrode and a second electrode alternating with each other, and a humidity sensitive layer disposed on and between the first electrode and the second electrode.

The humidity sensitive layer may extend over a passivation layer disposed on the peripheral circuit region.

The reference capacitor may include a dielectric layer made of a material different from the humidity sensitive layer.

The reference capacitor may comprise a first electrode, a second electrode, and a dielectric layer disposed between the first electrode and the second electrode.

Another object of the present disclosure is to dispose a reference capacitor of a capacitor type humidity sensor at an arbitrary position under the sensing capacitor. Hence, it is easy to change a design of the humidity sensor. A capacitor type humidity sensor smaller than the typical capacitor type humidity sensor is manufactured.

Another object of the present disclosure is to minimize an influence due to a parasitic capacitance and a dispersion of a process can be minimized in regards to the reference capacitor to improve the accuracy.

Other features and aspects may be apparent from the following detailed description, the drawings, and the claims.

Throughout the drawings and the detailed description, unless otherwise described, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Unless indicated otherwise, a statement that a first layer is "on" a second layer or a substrate is to be interpreted as covering both a case where the first layer is directly in contact with the second layer or the substrate, and a case where one or more other layers are disposed between the first layer and the second layer or the substrate.

The spatially-relative expressions such as "below", "beneath", "lower", "above", "upper", and the like may be used to conveniently describe relationships of one device or elements with other devices or among elements. The spatially-relative expressions should be understood as encompassing the direction illustrated in the drawings, and other directions of the device in use or operation. Further, the device may be oriented to other directions and accordingly, the interpretation of the spatially-relative expressions is based on the orientation.

A structure of a humidity sensor is designed so that a reference capacitor is aligned under a sensing capacitor. The reference capacitor is provided as an MIM capacitor or a PIP capacitor, to reduce a size of the reference capacitor and a size of the humidity sensor. Further, an influence due to a parasitic capacitance and a dispersion of a process generated in the humidity sensor can be minimized. Various examples of capacitor type humidity sensors will be described in detail with reference to the accompanying drawings.

Figure 1:
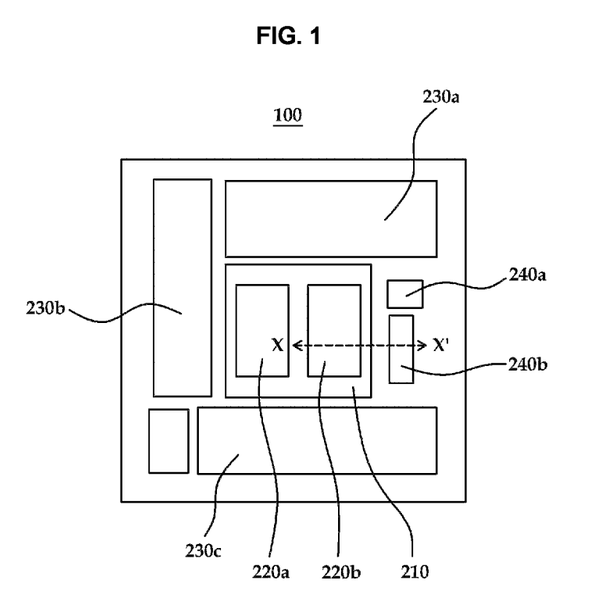
FIG. 1 is a diagram illustrating an example of a layout of a capacitor type humidity sensing chip.

Referring to FIG. 1, an example of a layout corresponding to a capacitor type humidity sensing chip or a humidity sensor 100 is illustrated. As illustrated in the example of FIG. 1, a humidity sensing region 210 using a humidity sensor is formed. Peripheral circuit regions 230a, 230b, 230c, 240a, and 240b are formed near the sensing region. The humidity sensing region 210 is a region in which moisture contained in the air is absorbed or attached to/detached from the region. In the process of packaging, the humidity sensing region is 210 exposed to external air. In the humidity sensing region 210, humidity sensing capacitor 220a and 220b are situated and a humidity sensing material is formed that can sense humidity. In this example, the humidity sensing region 210 includes two humidity sensing capacitors 220a and 220b of the same shape. This is to reduce the noise of the humidity sensor and to verify whether a measured capacitance value is reliable. A reliable value is obtained by comparing the capacitances measured in the two humidity sensing capacitors 220a and 220b and determining whether the capacitance values are similar. If a large difference is obtained as a humidity sensing output value, the value is not selected. In this way, it is possible to enhance the reliability of a sensing value measured by using the humidity sensing capacitor and to improve the accuracy of the humidity sensing capacitor. The examples of two humidity sensing capacitors 220a and 220b shown in FIG. 1 is only a non-exhaustive illustration, and other configurations of the humidity sensing capacitors 220a and 220b are considered to be well within the scope of the present disclosure.

The peripheral circuit regions 230a, 230b, 230c, 240a, and 240b surrounding the sensing region 210 include various circuits to process a digital signal. In a non-exhaustive example, a reference voltage block and a temperature sensing block may be disposed with respect to the circuit region 230a. Also, a Vdd power supply block (low dropout (LDO)), a gain control amp (GCA) block may be formed on the circuit region 230b. A logic circuit such as a digital filter, a digital signal processing (DSP) block, a signal control is situated with respect to the circuit region 230c. These circuits are electrically connected to the sensing region so that a signal is processed mutually and power input/output is facilitated with respect to an upper electrode and a bottom electrode that exist with respect to the sensing region.

The peripheral circuit region 230 includes MIM capacitors 240a and 240b used as a reference capacitor and a feedback capacitor (not illustrated). The detailed explanation is provided below with reference to FIGS. 4 and 5.

Figure 2:
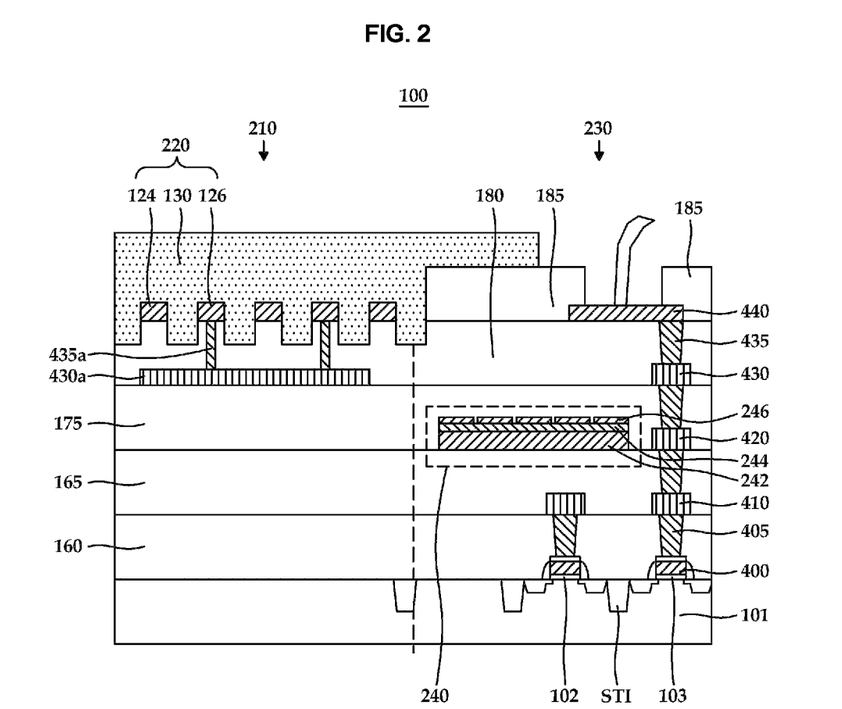
FIG. 2 is a diagram illustrating a first example of a cross-sectional view of a capacitor type humidity sensor.

FIG. 2 is a cross-sectional view taken along with line X-X' of FIG. 1, in which a capacitor type humidity sensor 100 of the first example is exhibited. As illustrated in the example of FIG. 2, a semiconductor substrate 101 is provided with respect to the capacitor type humidity sensor 100. One or more Metal-Oxide-Semiconductor Field-Effect Transistor (MOSFET) devices 102 and 103 are situated on the semiconductor substrate 101. However, the present examples are not limited to such MOSFET device. Other devices, such as, for example, a bulk isolated PN diode, an NPN bipolar transistor, and a laterally diffused metal oxide semiconductor (LDMOS) device may be similarly disposed. Interlayer insulating layers 160, 165, 175, and 180 are disposed on the MOSFET device. Metal wirings 410, 420, 430, and 440 are formed in the interlayer insulating layers 160, 165, 175, and 180. A contact plug 405 or a Via 435 connects each wiring.

The semiconductor substrate 101 is divided into a humidity sensing region 210 and a peripheral circuit region 230. As discussed above, the humidity sensing region 210 is responsive to the humidity of the air, and a capacitance value changes. The peripheral circuit region 230 acts as a signal processor to process a detected signal by the humidity sensing region 210 and to output a signal corresponding to the humidity.

A sensing capacitor 220 is formed at an upper surface of the interlayer insulating layer 180 on the humidity sensing region 210. The sensing capacitor 220 includes a first electrode 124, a second electrode 126 and a humidity sensitive layer 130. The first electrode 124 and the second electrode 126 are situated alternately. An insulating layer such as a silicon nitride layer (not illustrated) is formed on the first electrode 124 and the second electrode 126 to protect the electrode from moisture. The second electrode 126 is connected to the sensing metal wiring 430a by means of a Via 435a. The sensing metal wiring 430a, the Via 435a, the metal wiring 430, and the Via 435 of the peripheral circuit region 230 are formed at the same time. The humidity sensitive layer 130 is formed between the first electrode 124 and the second electrode 126 and around the electrodes. In this non-exhaustive example, the humidity sensitive layer 130 extends to an upper portion of a passivation layer 185 of the peripheral circuit region 230. It is beneficial to sense a change in humidity because many sensing areas formed of the humidity sensitive layer can be obtained accordingly. As a sensing area exposed to atmosphere increases, the amount of gas adsorption into the humidity sensitive layer increases. The humidity sensing capability having a larger sensing area is enhanced rather than smaller sensing area. Mostly, the passivation layer 185 is formed in the peripheral circuit region. The passivation layer 185 prevents the metal wirings 440 and 430 from being permeated by the external moisture. The humidity sensitive layer 130 may also be formed under a bottom surface of the first electrode 124 to increase the sensitivity.

A dielectric constant of the humidity sensitive material, such as, for example, a polymer, a polyimide, a porous ceramic, changes according to a relative humidity with respect to the humidity sensitive layer 130. These humidity sensitive materials absorb or release moisture according to the relative humidity when they are exposed to air. The dielectric constant that changes with the moisture content inside the humidity sensitive material is measured to detect the humidity. The sensing capacitor 220 provides a sensing capacitance value (Cs) measured by using a humidity sensitive layer 130, i.e., a sensing film.

As discussed above, a sensing capacitor 220, a reference capacitor 240 and a feedback capacitor (not illustrated) are situated with respect to the peripheral circuit region 230. The reference capacitor 240 provides a reference capacitance value (Cr). The reference capacitor 240 includes a dielectric layer made of different materials from the humidity sensitive layer 130 that is used to the sensing capacitor 220. The sensing capacitance value (Cs) changes according to the change in humidity, however, the reference capacitance value (Cr) is constant regardless of the humidity change. Therefore, it is possible to provide a capacitance as a reference. In order to obtain a constant value regardless of the change in humidity, the moisture does not contact the reference capacitor 240. It is preferable that the reference capacitor is formed on a different plane from the sensing capacitor. If the reference capacitor and the sensing capacitor are coplanar the moisture of the air may be absorbed by the reference capacitor and change the capacitance of the reference capacitor. It is preferable that the reference capacitor is disposed under a reference surface of the sensing capacitor. Like the reference capacitor, the feedback capacitor is formed on a different plane from the sensing capacitor. It is preferable that the feedback capacitor is disposed under the reference surface on which the sensing capacitor is formed.

The feedback capacitor includes a dielectric layer made of different materials from the humidity sensitive layer 130 and provides a feedback capacitance (Cf) value. The feedback capacitor acts to accumulate a charge that corresponds to capacitance differences (Cs−Cr) generated in the sensing capacitor 220 and the reference capacitor 240 respectively. A voltage corresponding to the charge accumulated in proportion to a drive voltage (VD) applied to the sensing capacitor 220 is outputted as an output voltage (VMEAS) through an output terminal. The output voltage (VMEAS) is derived by VMEAS=VD*(Cs−Cr)/Cf.

In a non-exhaustive example, a reference capacitor 240 or a feedback capacitor is formed on an arbitrary layer disposed with respect to the peripheral circuit region 230. The sensing capacitor 220 and the reference capacitor 240 are capacitor type humidity sensors that are aligned on different planes. The reference capacitor 240 is a capacitor type humidity sensor formed at a location lower than a location of the sensing capacitor 220. The reference capacitor 240 and the feedback capacitor may be any one of a metal-insulator-metal (MIM) capacitor or a polysilicon-insulator-polysilicon (PIP) capacitor. Hereinafter, an example in which the MIM capacitor is used as a reference capacitor 240 will be discussed. The advantage of using the MIM capacitor is that a designer may explore the options of changing a reference capacitance by his/her own initiative.

Figure 3:
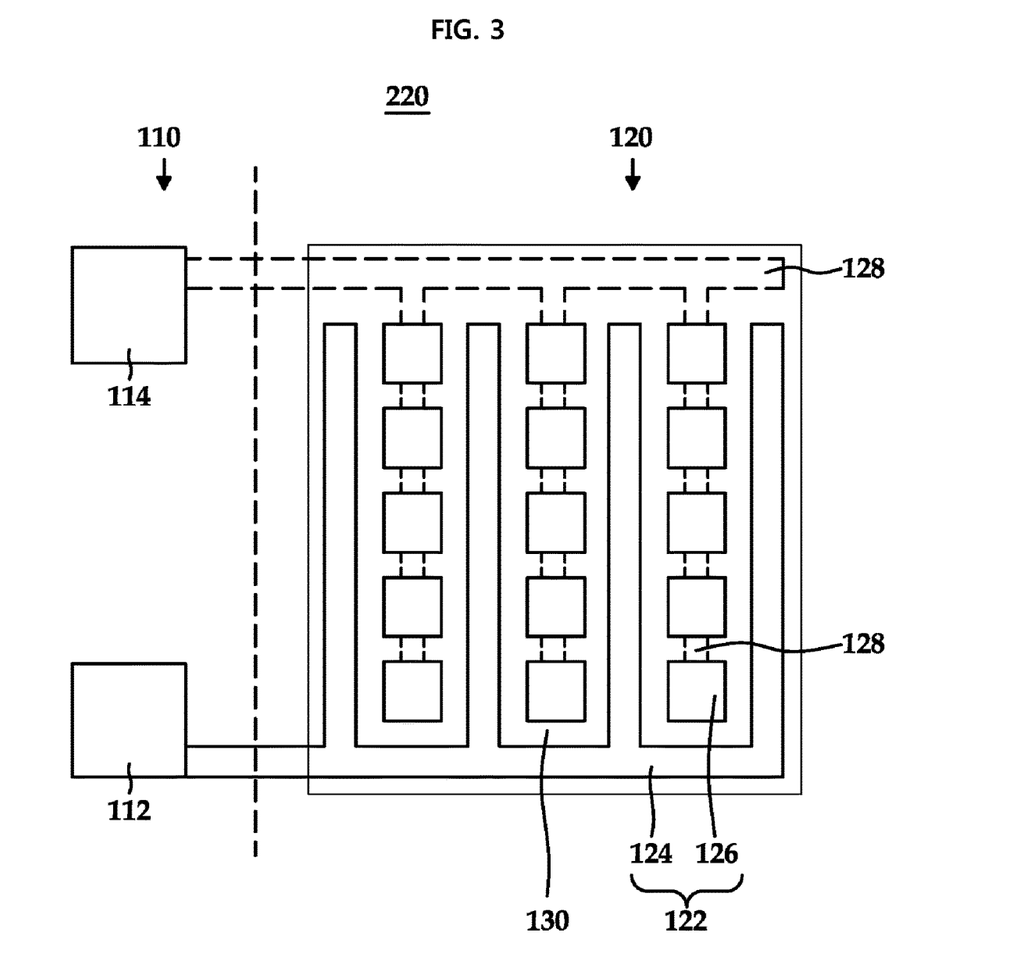
FIG. 3 is a diagram illustrating an example of a plan view of a capacitor type humidity sensing capacitor.

FIG. 3 illustrates an example of a plan view of the capacitor type humidity sensing capacitor 220 provided in the example of FIG. 2. The capacitor type humidity sensing capacitor 220 is divided into a pad portion 110 and a detector 120. The pad portion 110 consists of a first pad 112 for an upper electrode and a second pad 114 for a bottom electrode 128. Another pad (not illustrated) is situated under the second pad 114. The two pads are aligned in a perpendicular direction. The first pad 112 and the second pad 114 act to connect the detector 120 with an external circuit so that a signal detected by the detector 120 may be delivered to an external circuit (not illustrated). The detector 120 includes electrodes 122 and a humidity sensitive layer 130. The electrodes 122 include an upper electrode consisting of a first electrode 124 and a second electrode 126, and a bottom electrode 128 disposed under the second electrode 126. Both the upper electrode and the bottom electrode 128 are manufactured of a material in which electron flows without restriction. They may also be manufactured using a corrosion-resistant material.

Meanwhile, the first electrode 124 is formed in a stripe shape and the sections of second electrode 126 are square shapes situated in rows between the stripes of the first electrodes 124. The square shapes of the second electrode 126 help to detect a change in capacitance by increasing an area in contact with the humidity sensitive layer 130 that exists near the second electrode 126. The first electrode 124 and the sections of second electrode 126 are isolated to form an electric field there between.

Figure 4A:
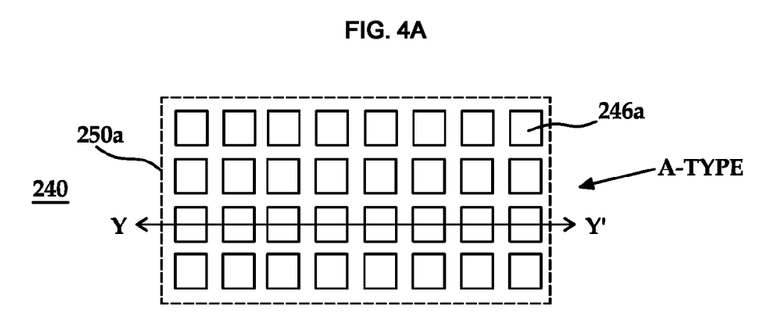
FIGS. 4A and 4B are diagrams illustrating an example of a plan view of a reference capacitor humidity sensor in the form of array.
Figure 4B:
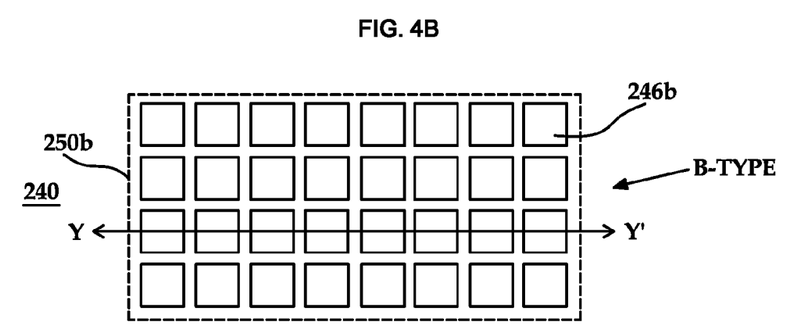

FIGS. 4A and 4B illustrate examples of a plan view of an array of an MIM capacitor used as a reference capacitor 240. The examples of FIGS. 4A and 4B describe square shaped unit capacitor areas 246a and 246b, respectively, which are arranged as an array to form A-type and B-type capacitors. The A-type capacitor and the B-type capacitor contain the individual unit capacitor areas 246a and 246b, respectively, having the overall capacitor area 250a and 250b, respectively. The unit capacitor area of B-type capacitor is designed to be larger than that of A-type capacitor (area 246a<246b). The overall capacitor area of B-type is designed to be larger than that of A type (area 250a<250b). The A type and the B-type capacitors can be electrically connected in parallel to each other based on the capacitance. In this example, a bigger capacitance is obtained when using the A-type and the B-type capacitors are connected in parallel than in using an A-type and a B-type separately. The different area with respect to the A-type capacitors and B-type capacitors is to obtain a target capacitance value in decimal point units. Two or more MIM capacitors array having different capacitor areas from each other may be aligned if necessary.

Figure 5A:
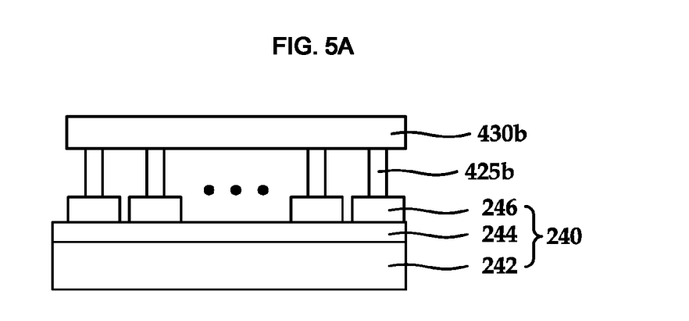
FIGS. 5A and 5B are diagrams illustrating an example of a cross-sectional view of a reference capacitor humidity sensor in the form of array.
Figure 5B:
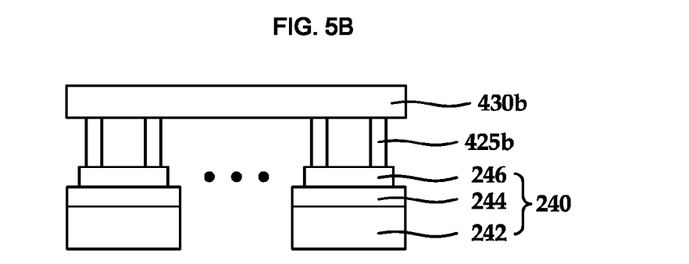

FIGS. 5A and 5B are examples of cross sectional view taken along with Line Y-Y' of FIGS. 4A and 4B, respectively. The reference capacitor 240 is a three-layered structure consisting of a bottom electrode 242, a dielectric layer 244, and an upper electrode 246. In this example, a metal pattern for wiring 420 may be used to the bottom electrode 242. That is, the bottom electrode is formed by the same process and material as the metal pattern for wiring 420 and materials, such as, for example, Aluminum (Al), Copper (Cu), or Al—Cu, may be used for the metal pattern for wiring 420. Different materials from the metal pattern for wiring 420 may be used to the upper electrode 246, such as, for example, a titanium nitride layer (TiN), a tantalum nitride layer (TaN), or a stacked layer in which a titanium nitride layer (TiN) is disposed on Aluminum.

As a non-exhaustive example, the titanium nitride layer (TiN) is used as the upper electrode 246 in the present examples because it is easy to etch to form an upper electrode. Further, an etch stop needed on a dielectric layer that exists under the TiN layer, and the etch selectivity of the titanium nitride layer is excellent in comparison with the dielectric layer.

A high-k Dielectric layer having a high dielectric constant such as, for example, a silicon nitride layer (SiNx), an aluminum oxide, or a hafnium oxide (HfOx) is used with respect to a dielectric layer 244 of an MIM capacitor. The dielectric layer of the sensing capacitor is a low-k dielectric layer having a low dielectric constant such as, for example, a polyimide. Thus, differences occur in a capacitance per unit area between a sensing capacitor and an MIM capacitor. The capacitance per unit area of the MIM capacitor differs in accordance with the materials and may approximately range from 1 to 10 fF/um$^2$. The capacitance per unit area of the sensing capacitor may range approximately from 0.001 to 0.1 fF/um$^2$. Because the capacitance per unit area of the MIM capacitor is higher than that of the sensing capacitor by at least one order of magnitude, an area of the MIM capacitor is relatively smaller than an area of the sensing capacitor.

As illustrated in the example of FIGS. 5A and 5B, there are two types of a reference capacitor 240. FIG. 5A illustrates an example of a reference capacitor in which a plurality of upper electrodes 246 are provided but a dielectric layer 244 and a bottom electrode 242 are formed as a long pattern. The upper electrodes 246 are connected to a metal interconnection 430b through Via 425b. Such structure is applicable to a situation in which a small area of a capacitance is provided. FIG. 5B illustrates an example of a reference capacitor in which an upper electrode 246, a dielectric layer 244 and a bottom electrode 42 are isolated from one another. At least two or more upper electrodes gather and form an upper electrode 246. The same structure applies to the dielectric layer and the bottom electrode. There are the plurality of dielectric layers and the plurality of bottom electrodes. Such structure is applicable to a situation where a bottom electrode is divided when a large area of a capacitor is needed. The number of the upper electrode 246 may vary. The size and the number of the upper electrode 246 may be altered according to the magnitude of capacitance of the reference capacitor 240. The reference capacitor 240 is formed on a plane on which the sensing capacitor 220 is not formed. In the same manner, the upper electrodes 246 are connected to a metal interconnection 430b through Via 425b.

The present example is configured such that the reference capacitor 240 is disposed at an arbitrary position under the sensing capacitor 220.

Other examples in which a reference capacitor 240 is disposed under the sensing capacitor 220 will be discussed. For ease of explanation, it is assumed that a semiconductor substrate described in the second to fourth examples is the same as a semiconductor substrate discussed in the first example, i.e., the substrate is partitioned into a humidity sensing region and a peripheral circuit region. A sensing capacitor is formed on the humidity sensing region. The inside of the semiconductor substrate is formed as being stacked, each layer of which is connected by means of Via according to a wiring form. The above descriptions of is also applicable to the second to fourth examples, and is incorporated herein by reference. Thus, the above description may not be repeated here. The present example discusses a position at which a reference capacitor is formed on a semiconductor substrate.

Figure 6:
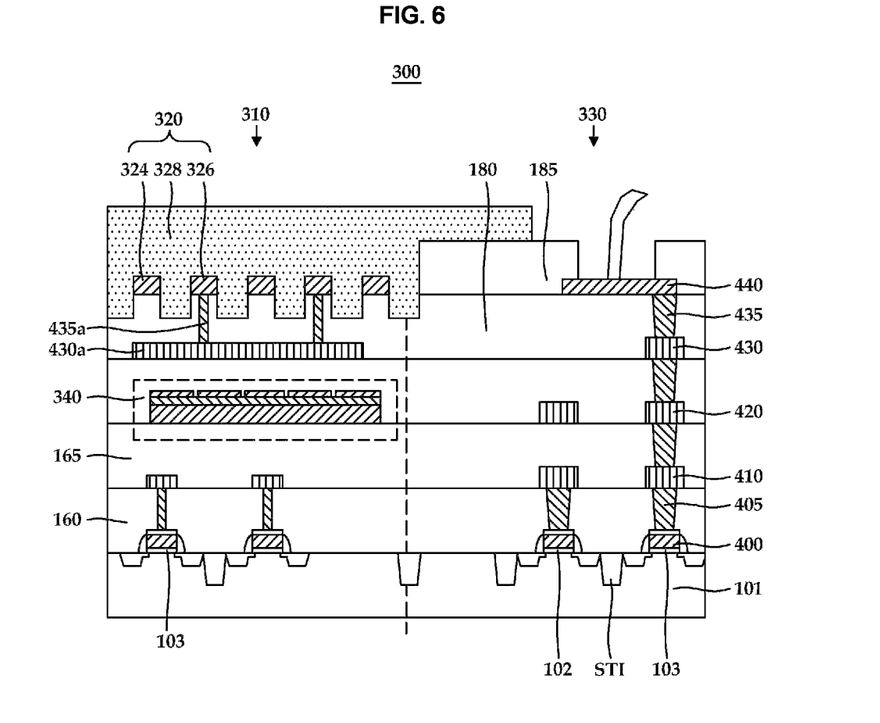
FIG. 6 is a diagram illustrating a second example of a cross-sectional view of a capacitor type humidity sensor.

FIG. 6 illustrates a cross sectional view of an example of a capacitor type humidity sensor illustrated in the second example. Referring to the second example, the reference capacitor 340 is not positioned in the peripheral region 330 but in the humidity sensing region 310. Both the sensing capacitor 320 and the reference capacitor 340 are positioned in the humidity sensing region 310. The reference capacitor 340 is situated under the sensing capacitor 320. In this configuration, a size or an area of a sensor chip can be markedly reduced. The reference capacitor 340 is formed as a capacitor of array form identical to the foregoing example. An MIM capacitor as a three-layer structure consisting of a bottom electrode, an insulating layer, and an upper electrode is applied with respect to the reference capacitor. In another non-exhaustive example, a polysilicon-insulator-polysilicon (PIP) capacitor instead of a metal-insulator-metal (MIM) capacitor may be used as a reference capacitor 340.

Figure 7:
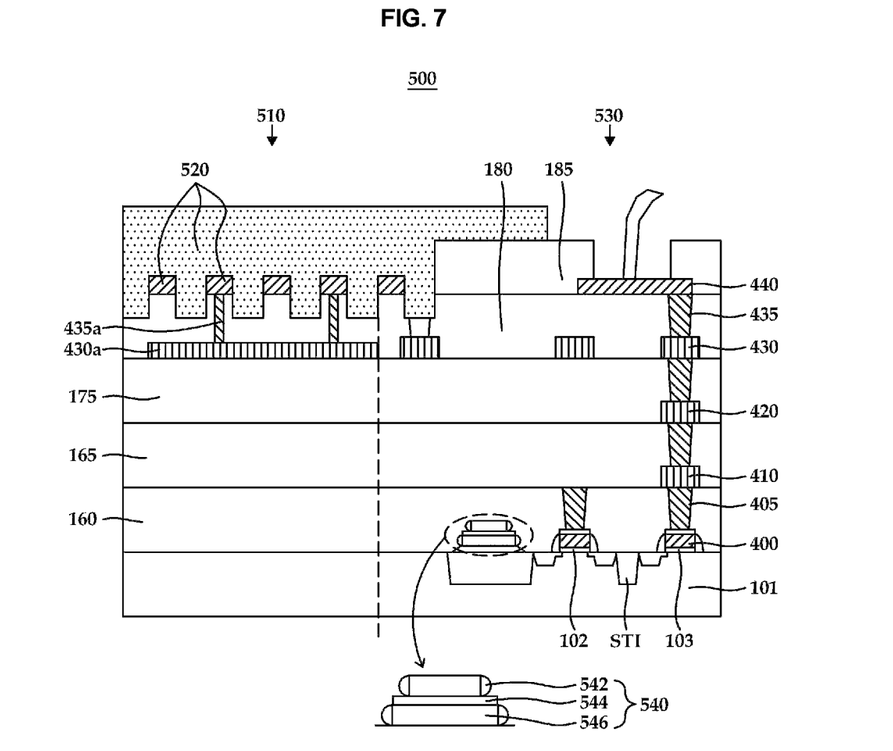
FIG. 7 is a diagram illustrating a third example of a cross-sectional view of a capacitor type humidity sensor.
Figure 8:
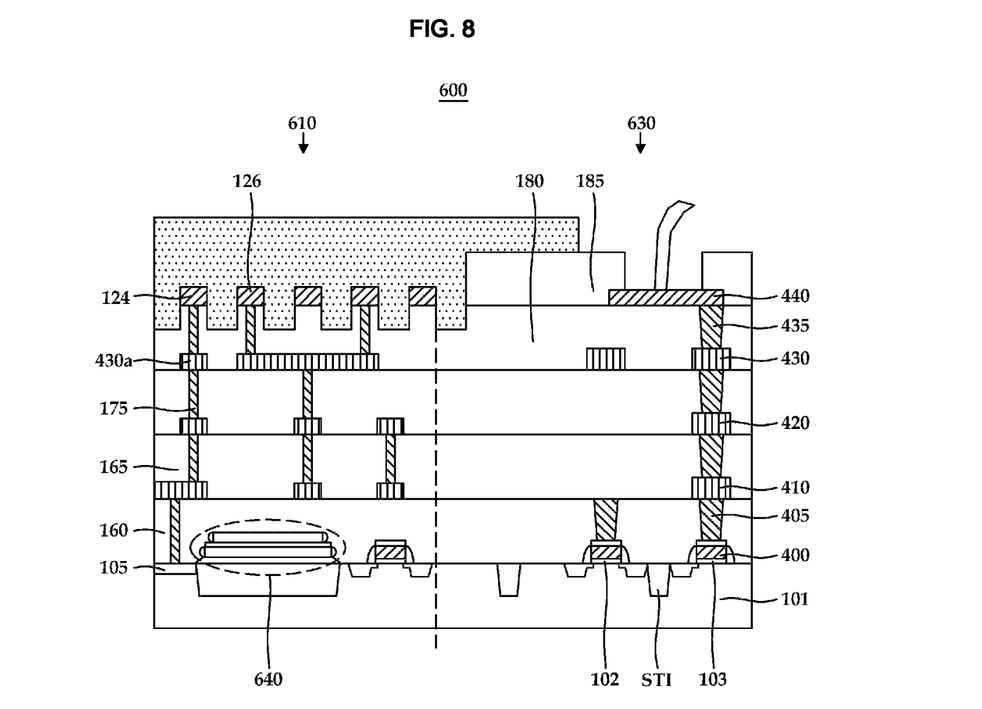
FIG. 8 is a diagram illustrating a fourth example of a cross-sectional view of a capacitor type humidity sensor.

Examples in which the PIP capacitor is used as a reference capacitor are illustrated in FIGS. 7 and 8. FIG. 7 illustrates a cross sectional view of a third example of a capacitor type humidity sensor. In the third example, a capacitor type humidity sensor 500 is configured such that a sensing capacitor 520 is formed on a humidity sensing region 510. A PIP capacitor 540 that operates as a reference capacitor is formed in the peripheral circuit region 530. A plurality of unit PIP capacitors 540 instead of one capacitor may be used to form the reference capacitor. The PIP capacitor 540 has an upper electrode and a bottom electrode consisting of polysilicon. Therefore, the overall structure is a three-layer structure consisting of an upper polysilicon 542, a dielectric layer 544, and a bottom polysilicon 546.

FIG. 8 is a cross-sectional view of a fourth example of a capacitor type humidity type. In this example, a reference capacitor 640 is formed in a humidity sensing region 610. A plurality of unit PIP capacitors 640 instead of one capacitor may be used to form the reference capacitor. The reference numeral 105 denotes a region of a high concentration.

As set out above, the capacitor type humidity sensor is characterized in that a reference capacitor is disposed on a plane on which a sensing capacitor is not formed among a humidity sensing region or a peripheral circuit region.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A capacitor type humidity sensor comprising:
    a semiconductor substrate comprising a humidity sensing region;
    a sensing capacitor, disposed in the humidity sensing region, comprising:
        a humidity sensitive layer;
        upper electrodes comprising a first electrode and a second electrode; and
        a bottom electrode disposed under, and connected to, the second electrode; and
    a reference capacitor comprising a first reference electrode and a second reference electrode,
    wherein a plurality of sections of the first reference electrode corresponds to a single section of the second reference electrode,
    the sensing capacitor and the reference capacitor are disposed on different planes from each other, and
    the humidity sensitive layer is disposed on and between the first electrode and the second electrode.

2. The sensor of claim 1, wherein the reference capacitor is aligned under the sensing capacitor.

3. The sensor of claim 1, wherein the reference capacitor comprises an MIM (metal insulator metal) capacitor in the form of an array.

4. The sensor of a claim 1, wherein the reference capacitor comprises a PIP (polysilicon insulator polysilicon) capacitor in the form of an array.

5. The sensor of claim 1, further comprising a feedback capacitor configured to provide a feedback capacitance value ($C_f$), wherein a dielectric layer of the feedback capacitor is made of a different material from the humidity sensitive layer.

6. The sensor of claim 5, wherein the feedback capacitor is configured to accumulate a charge that corresponds to capacitance differences ($C_s$–$C_r$) generated in the sensing capacitor ($C_s$) and the reference capacitor ($C_r$).

7. The sensor of claim 1, wherein the humidity sensitive layer extends to an upper portion of a passivation layer disposed on the substrate.

8. The sensor of claim 1, wherein the humidity sensitive layer is exposed to the atmosphere.

9. The sensor of claim 1, wherein the first reference electrode comprises a first material and the second reference electrode comprises a second material, and wherein the first material is different than the second material.

10. The sensor of claim 1, wherein the first electrode has a stripe shape and the second electrode has a square shape.

11. The sensor of claim 1, wherein the humidity sensitive layer comprises a region disposed below a bottom surface of the first electrode.

12. A humidity sensor comprising two capacitor type humidity sensors of claim 1.

13. A capacitor type humidity sensor comprising:
    a humidity sensing region comprising a humidity sensitive layer;
    a sensing capacitor, disposed in the humidity sensing region, comprising a first electrode and a second electrode disposed on a first plane; and
    a reference capacitor, disposed on a different plane than the sensing capacitor, comprising a top electrode, a bottom electrode, and a dielectric layer disposed between the top electrode and the bottom electrode,
    wherein a plurality of sections of the top electrode corresponds to a single section of the bottom electrode.

14. The sensor of claim 13, wherein the capacitor type humidity sensor further comprises a peripheral circuit region, and wherein the peripheral circuit region is configured to process a signal detected by the humidity sensing region to output a detected humidity.

15. The sensor of claim 14, wherein the peripheral circuit region comprises a reference voltage block, a temperature sensing block, a Vdd power supply block, a gain control amp (GCA) block, and at least one signal control block.

16. The sensor of claim 13, wherein the sensing capacitor further comprises:
    a Via connecting to the second electrode; and
    a lower metal wire disposed on a second plane below the first plane, wherein the lower metal wire connects to the Via, and
    wherein the humidity sensitive layer is disposed adjacent to the Via.

17. The sensor of claim 13, wherein the humidity sensitive layer extends over a passivation layer disposed on the reference capacitors.

18. The sensor of claim 13, wherein the dielectric layer is made of a material different from the humidity sensitive layer.

19. The sensor of claim 13, wherein the top electrode is disposed on a third plane and the bottom electrode is disposed on a fourth plane below the third plane.

20. The sensor of claim 13, wherein a direction of separation of opposing electrodes of the sensing capacitor is transverse to a direction of separation of opposing electrodes of the reference capacitor.

21. A capacitor type humidity sensor, comprising:
a humidity sensing region comprising a humidity sensitive layer;
a sensing capacitor disposed in the humidity sensing region; and
a reference capacitor, comprising:
plural upper electrodes;
a bottom electrode disposed below the plural upper electrodes; and
a dielectric layer disposed between lower surfaces of the plural upper electrodes and an upper surface of the bottom electrode.

22. The capacitor type humidity sensor of claim 21, wherein the reference capacitor further comprises vias connecting respective ones of the plural upper electrodes to a metal interconnection.

23. The capacitor type humidity sensor of claim 21, wherein the sensing capacitor comprises:
a first electrode; and
a second electrode,
wherein the humidity sensitive layer comprises a region disposed below a bottom surface of the first electrode.

24. The capacitor type humidity sensor of claim 21, wherein the reference capacitor includes a plurality of reference capacitors.

25. The capacitor type humidity sensor of claim 24, wherein each of the reference capacitors is square-shaped.

* * * * *